(12) United States Patent
Gong

(10) Patent No.: US 7,385,081 B1
(45) Date of Patent: Jun. 10, 2008

(54) TEREPHTHALIC ACID COMPOSITION AND PROCESS FOR THE PRODUCTION THEREOF

(75) Inventor: William H. Gong, Elmhurst, IL (US)

(73) Assignee: BP Corporation North America Inc., Warrenville, IL (US)

(*) Notice: Subject to any disclaimer, the term of this patent is extended or adjusted under 35 U.S.C. 154(b) by 0 days.

(21) Appl. No.: 11/940,097

(22) Filed: Nov. 14, 2007

(51) Int. Cl.
*C07C 63/00* (2006.01)
(52) U.S. Cl. ........................... 562/405; 549/200
(58) Field of Classification Search ........ 562/405; 549/200
See application file for complete search history.

(56) References Cited

U.S. PATENT DOCUMENTS 3,265,762 A * 8/1966 Quisenberry ............ 525/444
3,326,944 A * 6/1967 Lew ........................ 549/485

* cited by examiner

*Primary Examiner*—Yvonne Eyler
*Assistant Examiner*—Sudhakar Katakam
(74) *Attorney, Agent, or Firm*—Kelly L. Cummings

(57) ABSTRACT

Terephthalic acid is prepared by reacting a 2,5-furandicarboxylate with ethylene in the presence of a solvent to produce a bicyclic ether; and then dehydrating the bicyclic ether. The process of the present invention effectively produces terephthalic acid, while reducing or eliminating the impurities, color bodies and carbon oxides produced in commercial practice by the liquid-phase oxidation of methyl-substituted benzene feedstocks.

18 Claims, No Drawings

TEREPHTHALIC ACID COMPOSITION AND PROCESS FOR THE PRODUCTION THEREOF

FIELD OF THE INVENTION

This invention relates generally to terephthalic acid and, more particularly, to a new terephthalic acid composition and a process for the production of terephthalic acid from a 2,5-furandicarboxylate.

BACKGROUND OF THE INVENTION

Terephthalic acid and other aromatic carboxylic acids are widely used in the manufacture of polyesters, commonly by reaction with ethylene glycol, higher alkylene glycols or combinations thereof, for conversion to fiber, film, containers, bottles and other packaging materials, and molded articles.

In commercial practice, aromatic carboxylic acids are commonly made by liquid-phase oxidation in an aqueous acetic acid solvent of methyl-substituted benzene and naphthalene feedstocks, in which the positions of the methyl substituents correspond to the positions of carboxyl groups in the desired aromatic carboxylic acid product, with air or another source of oxygen, which is normally gaseous, in the presence of a bromine-promoted catalyst comprising cobalt and manganese ions. The oxidation is exothermic and yields aromatic carboxylic acid together with high- and low-molecular weight byproducts, including partial or intermediate oxidation products of the aromatic feedstock, and acetic acid decomposition reaction products, such as methanol, methyl acetate, and methyl bromide. Water is also generated as a byproduct. Aromatic carboxylic acids, typically accompanied by oxidation byproducts of the feedstock, are commonly formed dissolved or as suspended solids in the liquid-phase reaction mixture and are commonly recovered by crystallization and solid-liquid separation techniques.

The exothermic oxidation reaction is commonly conducted in a suitable reaction vessel at elevated temperature and pressure. A liquid-phase reaction mixture is maintained in the vessel and a vapor phase formed as a result of the exothermic oxidation is evaporated from the liquid phase and removed from the reactor to control reaction temperature. The vapor phase comprises water vapor, vaporized acetic acid reaction solvent and small amounts of byproducts of the oxidation, including both solvent and feedstock byproducts. It usually also contains oxygen gas not consumed in the oxidation, minor amounts of unreacted feedstock, carbon oxides and, when the oxygen source for the process is air or another oxygen-containing gaseous mixture, nitrogen and other inert gaseous components of the source gas.

The high temperature and pressure vapor phase generated by the liquid-phase oxidation is a potentially valuable source of recoverable acetic acid reaction solvent, unreacted feed material and reaction byproducts, as well as energy. However, its substantial water content, high temperature and pressure and corrosive nature due to components such as gaseous methyl bromide, acetic acid solvent and water pose technical and economic challenges to separating or recovering components for recycle and recovering its energy content. Further, impurities that remain unseparated in recovered process streams can prevent re-use of streams if impurities adversely affect other process aspects or product quality.

Purified forms of aromatic carboxylic acids are usually favored for the manufacture of polyesters for important applications, such as fibers and bottles, because impurities, such as the byproducts generated from the aromatic feedstocks during oxidation and, more generally, various carbonyl-substituted aromatic species, are known to cause or correlate with color formation in polyesters made from the acids and, in turn, off-color in polyester converted products.

Preferred purified forms of terephthalic acid and other aromatic carboxylic acids with lower impurities contents, such as purified terephthalic acid or "PTA", are made by catalytically hydrogenating less pure forms of the acids, such as crude product comprising aromatic carboxylic acid and byproducts generated by the liquid-phase oxidation of the aromatic feedstock or so-called medium purity products, in solution at elevated temperature and pressure using a noble metal catalyst. Purification not only removes impurities from the crude and medium purity products, particularly the major impurity, 4-carboxybenzaldehyde, but also reduces the level of color bodies and the amount of metals, acetic acid and bromine compounds. In commercial practice, liquid-phase oxidation of alkyl aromatic feed materials to crude aromatic carboxylic acid and purification of the crude product are often conducted in continuous integrated processes in which crude product from liquid-phase oxidation is used as the starting material for purification.

Reducing or eliminating the production of impurities, color bodies and carbon oxides from such commercial processes continues to be an ongoing challenge. One solution may be found in an alternative process for the manufacture of aromatic carboxylic acids from feedstocks other than methyl-substituted benzene and naphthalene feed materials.

The U.S. Department of Energy ("DOE") has recently identified 12 top-tier chemical building blocks from biomass processing, as reported in the Biomass Report for the DOE Office of Energy Efficiency and Renewable Energy entitled *Top Value Added Chemicals from Biomass, Volume 1—Results of Screening for Potential Candidates from Sugars and Synthesis Gas, August* 2004. Among the twelve building blocks identified by the DOE is 2,5-furandicarboxylic acid. The DOE has been soliciting proposals for the use of 2,5-furandicarboxylic acid in the production of commodity chemicals, such as polyesters.

It is generally known that biomass carbohydrates can be enzymatically converted to fructose and other sugars. Under facile dehydration conditions, these sugars are then converted to 5-hydroxymethylfurfural, which is readily oxidized to 2,5-furandicarboxylic acid. It has been reported that of the approximately 200 billion tons of biomass produced per year, 95% of it is in the form of carbohydrates, and only 3 to 4% of the total carbohydrates are currently being used for food and other purposes. Thus, there is an abundant untapped supply of biomass carbohydrates, which can potentially be used for the production of non-petroleum based commodity chemicals that are fully renewable.

Accordingly, it would be desirable to provide a process for the production of terephthalic acid from a feedstock other than a conventional alkyl aromatic feed material, such as paraxylene, which not only reduces or eliminates the production of impurities, color bodies and carbon oxides, but also eliminates the need for the purification step in current commercial processes. It would also be desirable if the alternative feedstock utilized in the process was derived from biomass.

SUMMARY OF THE INVENTION

The process of the invention, in its embodiments and features, calls for reacting a 2,5-furandicarboxylate with ethylene in the presence of a solvent to produce a bicyclic ether; and then dehydrating the bicyclic ether.

In one embodiment of the invention, the 2,5-furandicarboxylate is derived from biomass whereby enzymatic or microbial degradation occurs from biomass carbohydrates to produce fructose, sucrose and mixtures thereof, the sugars are then converted to 5-hydroxymethylfurfural, and the 5-hydroxymethylfurfural is readily oxidized to 2,5-furandicarboxylate.

The inventive process efficiently and effectively produces terephthalic acid with purity comparable to conventional PTA purified by hydrogenation of crude product from par-axylene oxidation, while reducing or eliminating the resultant impurities, color bodies and carbon oxides produced in commercial practice by the liquid-phase oxidation of methyl-substituted benzene feedstocks.

In another aspect, the invention provides a terephthalic acid composition comprising a minor amount of 2,5-furandicarboxylic acid as an impurity wherein the terephthalic acid has a ratio of carbon-14 isotope to carbon-12 isotope of about $1.5 \times 10^{-12}$ to 1.

The invention also provides a terephthalic acid composition having a purity sufficient for direct conversion by reaction with at least one glycol to polyester suitable for the manufacture of fiber and film without additional purification comprising less than about 25 ppm of 2,5-furandicarboxylic acid as an impurity.

DETAILED DESCRIPTION OF THE INVENTION

The present invention is directed to a process for producing terephthalic acid (TA) and to a new TA composition. In accordance with this invention, a 2,5-furandicarboxylate is reacted with ethylene in the presence of a solvent to produce a bicyclic ether, and then the bicyclic ether is dehydrated. The resultant TA has a purity comparable to conventional PTA purified by hydrogenation of crude product from par-axylene oxidation and sufficient for direct conversion to fiber and film.

In accordance with one embodiment, the 2,5-furandicarboxylate is derived from biomass. "Biomass" is generally defined as plant material, vegetation or agricultural waste used as a fuel or energy source. The ratio of carbon-14 isotope to carbon-12 isotope for biomass carbon is generally known to those skilled in the art to be about $2 \times 10^{-12}$ to 1 based on the current natural abundance of carbon-14 to carbon-12 as taken from air samples.

When 2,5-furandicarboxylate derived from biomass is utilized in the practice of the invention, the resultant TA will have a ratio of carbon-14 isotope to carbon-12 isotope of about $1.5 \times 10^{-12}$ to 1, or 12 disintegrations per minute per gram of carbon, as measured on a Geiger counter.

Furthermore, unlike conventional PTA produced from an alkyl aromatic feedstock derived from petroleum refining, the TA composition derived from biomass in accordance with the present invention contains a minor amount of 2,5-furandicarboxylic acid (FDCA) as an impurity and is free of contaminants, such as 4-carboxybenzaldehyde, and color bodies. The amount of FDCA present in the TA composition derived from biomass is typically at least about 10 ppm, as determined by high pressure liquid chromatography. The maximum amount of FDCA in the TA composition is preferably less than about 25 ppm. It is desirable to limit impurities in TA compositions that are to be used in the manufacture of polyester to avoid altering the physical or mechanical properties. Thus, if desired, the FDCA impurity level can be reduced by crystallization with a solvent such as water. The inventive TA composition, however, has a purity sufficient for direct conversion by reaction with at least one glycol to polyester suitable for the manufacture of fiber and film without the need for any additional purification.

In one aspect of the current invention, the 2,5-furandicarboxylate that may be used is FDCA. It is generally known to those skilled in the art that enzymatic or microbial degradation occurs from biomass to produce a mixture of fructose and sucrose. Biomass can also be converted to sugars by a two-stage hydrolysis process as described in U.S. Pat. No. 4,427,453, which is incorporated herein by reference. In the first stage, the biomass is crushed and treated with dilute mineral acid at a temperature of about 135° C. to 190° C. under a pressure sufficient to maintain a liquid mixture for about 0.05 to 20 minutes. In the first stage, mainly hemicellulose and some cellulose are hydrolyzed to sugars. The reaction vessel is then rapidly depressurized to flash off the hydrolysate. Next, the residue is treated again in the second stage with dilute mineral acid, heated to about 210° C. to 250° C. and pressurized to maintain a liquid phase for about 0.05 to 20 minutes. The reactor is then rapidly depressurized to flash off the hydrolysate to produce the sugars.

A reaction of these sugars with an acid catalyst then results in 5-hydroxymethyl-2-furfural (HMF) via a dehydrocyclization, as described in Zhao et al., *Science*, Jun. 15, 2007, 316, 1597-1600; and Bicker et al., *Green Chemistry*, 2003, 5, 280-284, which are incorporated herein by reference. In Zhao et al., the sugar is treated with a metal salt such as chromium (II) chloride in the presence of an ionic liquid at 100° C. for three hours to result in 70% yield of HMF. In Bicker et al., sugars are dehydrocyclized to HMF by the action of sub- or super-critical acetone as the solvent and sulfuric acid as the catalyst, at temperature greater than 180° C. for about two minutes to yield HMF at nearly 70% selectivity.

The HMF is then readily oxidized to FDCA, as described by Merat et al. in FR 2669634, which is incorporated herein by reference. In Merat et al., a platinum-lead catalyst is used in the presence of oxygen and aqueous alkaline conditions to oxidize HMF to FDCA at room temperature (approximately 25° C.) for two hours to achieve a complete conversion of the HMF, and an FDCA yield after acidification of 94%, with a purity of about 99%.

In another embodiment of the invention, FDCA may be synthesized by any conventional method from a non-biomass source, such as by the in situ oxidation of HMF as described in Kroger et al., *Topics in Catalysis*, 2000, 13, 237-242; the oxidation by silver-copper reagent, as described in U.S. Pat. No. 3,326,944; and the electrochemical oxidation to FDCA, as discussed by Grabowski et al., PL 161831, which are incorporated herein by reference. Such a non-biomass source may include, but is not limited to, 2,5-dimethylfuran.

Suitable solvents which may be used in the practice of the invention with FDCA include water, dimethylsulfoxide, N-methyl-2-pyrrolidinone, N,N-dimethylformamide, $C_1$ to $C_{10}$ alcohols, $C_2$ to $C_6$ ketones, and $C_2$ to $C_{10}$ esters. Water is the preferred solvent. Additives, such as alkaline and alkaline earth metal hydroxides, may also optionally be used in the water to convert the FDCA into more water-soluble salts and enhance the reactivity of the FDCA. Suitable alkaline and alkaline earth metal hydroxides include sodium, potassium and calcium hydroxides. The concentration of FDCA in the solvent is typically in the range of about 5 to about 20 weight percent FDCA.

When FDCA is reacted with ethylene in the presence of a solvent, the intermediate, bicyclic ether that is produced is 7-oxa-bicyclo[2.2.1]hept-2-ene-1,4-dicarboxylic acid. Ethylene may be sparged or bubbled into a solution of FDCA. The amount of ethylene should be in excess of the amount of FDCA and preferably, at least 2 moles of ethylene per mole of FDCA.

In another aspect of the present invention, the 2,5-furandicarboxylate that may be used is dimethyl 2,5-furandicarboxylate (DM FDCA), i.e., a dimethyl ester derivative of FDCA. Typically, DM FDCA can be derived by a reaction of FDCA and methanol in the presence of a protic acid catalyst, such as concentrated sulfuric or phosphoric acid. The FDCA is combined with methanol and phosphoric acid, and then heated to approximately 200° C. under pressure to maintain a liquid phase for about six to nine hours.

Suitable solvents which may be used in the practice of the invention with DM FDCA include aromatic hydrocarbons, dimethylsulfoxide, N-methyl-2-pyrrolidinone, N,N-dimethylformamide, $C_1$ to $C_{10}$ alcohols, $C_2$ to $C_6$ ketones, and $C_2$ to $C_{10}$ esters. Toluene is a preferred solvent. The activity of the reaction may be further enhanced by the addition of a catalytic amount of Lewis acids, such as aluminum, boron, zinc or titanium salts, in the range of about 5 ppm to about 2000 ppm.

When DM FDCA is reacted with ethylene in the presence of a solvent, the intermediate, bicyclic ether that is produced is dimethyl 7-oxa-bicyclo[2.2.1]hept-2-ene-1,4-dicarboxylate.

In another aspect of the present invention, the 2,5-furandicarboxylate that may be used is a mixture of FDCA and DM FDCA. Suitable solvents which may be used in the practice of the invention with the FDCA and DM FDCA mixture include water, aromatic hydrocarbons, dimethylsulfoxide, N-methyl-2-pyrrolidinone, N,N-dimethylformamide, $C_1$ to $C_{10}$ alcohols, $C_2$ to $C_6$ ketones, $C_2$ to $C_{10}$ esters, and mixtures thereof.

The combination of the 2,5-furandicarboxylate and ethylene in the presence of a solvent promotes a Diels Alder reaction to produce the intermediate, bicyclic ether. The intermediate bicyclic ether is 7-oxa-bicyclo[2.2.1]hept-2-ene-1,4-dicarboxylate.

When the intermediate, bicyclic ether is produced, a spontaneous dehydration reaction of the bicyclic ether will occur if the temperature from the reaction of FDCA with ethylene is maintained so that the heat of reaction is sufficient to drive the dehydration. A preferred temperature at which the reaction system is maintained in order to drive the dehydration is at least about 100° C. and, more preferably, about 200° C. This spontaneous dehydration allows for the production of TA from the 2,5-furandicarboxylate in one step, i.e., the TA can be produced in a single reactor since the dehydration of the bicyclic ether can be caused to occur automatically without having to isolate the bicyclic ether in a separate vessel.

In another aspect of the present invention, the bicyclic ether may be isolated by any conventional method, such as filtration, and then dehydrated via an acid-catalyzed dehydration reaction by dissolving the bicyclic ether in a solvent such as acetic acid and heating to boil, to enhance the ease of purification of the final TA product. The acid-catalyzed dehydration reaction is generally known to those having ordinary skill in the art to which this invention pertains. The purification may be performed by recrystallization from a solvent, such as water, in which the TA is soluble, as well as by other known procedures.

The temperature of both the reaction of the 2,5-furandicarboxylate with ethylene and the dehydration of the bicyclic ether should be maintained in the range of about 100° C. to about 250° C. and, preferably, in the range of about 180° C. to about 210° C. The ethylene is reacted with the 2,5-furandicarboxylate at a pressure in the range of about 10 pounds per square inch gauge (psig) to about 2000 psig. More preferably, the ethylene pressure is in the range of about 50 psig to about 1000 psig, with about 100 psig to about 300 psig being most preferred. The 2,5-furandicarboxylate should be reacted for about 60 minutes to about 480 minutes and, preferably, for about 90 minutes to about 120 minutes.

The TA may be recovered by cooling the reaction mixture to ambient temperature, and then filtering the solids from the supernatant.

The process of the present invention effectively produces TA without the use of a conventional alkyl aromatic feedstock, such as paraxylene. By reacting a 2,5-furandicarboxylate with ethylene in the presence of a solvent to produce a bicyclic ether; and then dehydrating the bicyclic ether, the inventor has surprisingly discovered that a high purity TA composition is produced. In fact, the purity of the TA is comparable to that of conventional PTA purified by hydrogenation of crude product from paraxylene oxidation and is sufficient for direct conversion by reaction with at least one glycol to polyester suitable for the manufacture of fiber and film without the need for any additional purification.

Also, the inventive process does not produce partial oxidation products commonly generated as byproducts in conventional paraxylene oxidation processes. These byproducts include 4-carboxybenzaldehyde and other contaminants, such as p-toluic acid, p-tolualdehyde, and benzoic acid, all of which are commonly found in commercial PTA processes. Carbon oxides normally associated with the decomposition of acetic acid are also substantially absent (i.e., there may be trace levels of carbon dioxide produced from a decarboxylation reaction of the 2,5-furandicarboxylate) from the current process, as are the color bodies produced during the liquid-phase oxidation of paraxylene.

Additionally, utilizing a 2,5-furandicarboxylate as an alternative feedstock in the present invention allows for the production of TA without the use of acetic acid, catalysts or oxygen, all of which are found in conventional PTA processes. It should be noted that although catalysts are not required in the practice of this invention, non-conventional catalysts having Lewis acidity including, but not limited to, zinc (II) salts, such as zinc (II) acetate or bromide, and iron (III) salts, such as iron (III) acetate, may be used to improve reaction rates. Moreover, utilizing a 2,5-furandicarboxylate allows for the use of a renewable feedstock for the production of TA.

Furthermore, the TA composition of the present invention simplifies or eliminates the conventional purification steps which typically utilize expensive palladium catalysts.

EXAMPLES

The following examples are intended to be illustrative of the present invention and to teach one of ordinary skill how to make and use the invention. These examples are not intended to limit the invention or its protection in any way.

Example 1

5 grams of FDCA (available from the Atlantic Chemical Company) and 100 grams of distilled and deionized (D&D) water were combined in an autoclave and then pressurized with ethylene and heated for 120 minutes. After the reaction time elapsed, the unit was cooled and depressurized, and the reaction mixture (i.e., a mixture of solids covered by the reaction solvent, which is known as the "mother liquor") was collected. This mixture was then separated by filtration to yield a filtered cake (i.e., solids) and the mother liquor. Both the filtered cake and mother liquor were analyzed by high pressure liquid chromatography (HPLC).

As shown below in Table 1, as the reaction conditions were made more severe by increasing the temperature and pressure, not only was TA produced in one step, i.e., in a single reactor vessel, but its yield was also increased. Under the mild conditions of Example No. 1A, where 100 psig ethylene was used at a temperature of 100° C., no TA was observed by HPLC analysis after 120 minutes. In Example No. 1B, increasing only the temperature to 150° C. did produce a trace concentration of TA in the mother liquor. By increasing only the pressure from 100 to 200 psig, while holding the temperature at 100° C. in Example No. 1C, the TA concentration in the mother liquor was increased. By further increasing the ethylene pressure and temperature in Example No. 1D to 200 psig and 200° C., respectively, the filtered cake was found to contain a measurable TA level of 372 ppmw. Lastly, in Example No. 1E, the FDCA charge was increased from 5 to 10 grams, and the ethylene pressure was further increased to 250 psig, while holding the temperature at 200° C. No insoluble solids were observed in the reaction mixture. A sample of the homogeneous liquid material was obtained and permitted to dry to leave behind solids that had once been soluble in the homogeneous liquid. The total solids concentration, which was determined by weighing the residue of the evaporated sample, dividing by the total weight of the mother liquor, and multiplying by 100, was 4.2785 wt %. Of the evaporated residue, it was found to contain 3,504 ppmw TA.

Based on these results and the amount of FDCA charged, it was estimated that the TA was made in 0.14 mol % yield. The presence of 7-oxa-bicyclo[2.2.1]hept-2-ene-1,4-dicarboxylic acid was also observed by HPLC analysis. Thus, as demonstrated in Table 1, the inventive process successfully produced TA from FDCA. In addition, because paraxylene was not used, the TA was produced in the absence of 4-carboxybenzaldehyde and color bodies normally associated with paraxylene oxidation.

Table 1

| | Example No. | | | | |
|---|---|---|---|---|---|
| | 1A | 1B | 1C | 1D | 1E |
| Reactor Charge (g) | | | | | |
| FDCA | 5 | 5 | 5 | 5 | 10 |
| D&D Water | 100 | 100 | 100 | 100 | 100 |
| Ethylene (psig) | 100 | 100 | 200 | 200 | 250 |
| Temperature (° C.) | 100 | 150 | 100 | 200 | 200 |
| Time (min) | 120 | 120 | 120 | 120 | 120 |
| Material Balance (%) | 88 | 82 | 81 | 103 | 94 |
| Products (ppmw) | | | | | |
| TA (mother liquor) | None | 0.801 | 4.56 | N/A | N/A |
| TA (filtered cake) | None | None | None | 372 | 3,504 |

Example 2

100 grams of FDCA, 800 grams of methanol, 9.41 grams of phosphoric acid (85%), and 1.26 grams of water were charged into a high pressure reactor equipped with a gas inlet and outlet. The reactor was sealed, filled and flushed with nitrogen nine times. The inlet and outlet were then closed and the reaction mixture was stirred and heated to 200° C. for nine hours. The reactor was cooled, vented, and 878.95 grams of the total reactor content were collected. A gas-chromatographic analysis was conducted on the solids to reveal the following gas chromatographic peak area percentages: 63% DM FDCA, 21% monomethyl FDCA, and 14.9% unreacted FDCA. There were 1.1% unknowns estimated to be present.

The DM FDCA was separated from the other components by filtration of the solids. The solids were washed twice with fresh methanol and then dried at 60° C. under a slight vacuum at 27 mmHg to produce about 44.813 grams of solids. This material was then analyzed by gas chromatography—mass spectrometry to reveal the following normalized peak areas: 95.0% DM FDCA, 3.2% monomethyl FDCA, and 1.90% FDCA.

5 grams of DM FDCA and 60.5 grams of toluene were added into a Parr reactor. The reactor was sealed and pressurized with ethylene to 250 psig. The mixture was heated with stirring to 120-125° C., and then held for about seven hours. The reactor was cooled and depressurized, and 60.125 grams of total reactor effluent were collected. The slurry was filtered, and the solids were initially dried overnight at 65 to 70° C. under ambient pressure, and then dried at 100° C. and under vacuum at 27 mmHg for 30 minutes. Analysis of the filtered solids revealed the following components and their corresponding concentrations in weight percent: 39.7% DM FDCA, 0.699% monomethyl FDCA, 0.011% FDCA, and 0.015% TA.

This procedure was repeated, except that the temperature was fixed at 190-195° C. for approximately five hours. Analysis of the solids revealed the following concentrations in weight percent: 39.1% DM FDCA, 0.547% monomethyl FDCA, 0.21% FDCA, and 0.021% TA.

Based on these results, the inventive process successfully produced TA from DM FDCA and, surprisingly, no dimethyl terephthalate was produced. One skilled in the art would have expected the dimethyl ester to remain as part of the molecule throughout the reaction sequence. In addition, because DM FDCA was used as the feedstock, rather than a conventional alkyl aromatic, the TA was produced in the absence of carbon oxides normally associated with solvent decomposition, impurities and color bodies. Furthermore, these findings revealed that FDCA can be used directly or as an ester derivative to produce the desired product, TA.

While the present invention is described above in connection with preferred or illustrative embodiments, these embodiments are not intended to be exhaustive or limiting of the invention. Rather, the invention is intended to cover all alternatives, modifications and equivalents included within its spirit and scope, as defined by the appended claims.

What is claimed is:

1. A process for the production of terephthalic acid comprising:
   a. reacting a 2,5-furandicarboxyate with ethylene in the presence of a solvent to produce a bicyclic ether; and
   b. dehydrating the bicyclic ether.

2. The process of claim 1 wherein the 2,5-furandicarboxylate is derived from biomass.

3. The process of claim 2 wherein the 2,5-furandicarboxylate is derived from biomass by the steps comprising:
   a. converting the biomass to a sugar comprising fructose, sucrose and mixtures thereof;
   b. converting the sugar to 5-hydroxymethylfurfural; and
   c. oxidizing the 5-hydroxymethylfurfural to 2,5-furandicarboxylate.

4. The process of claim 1 wherein the 2,5-furandicarboxyate is 2,5-furandicarboxylic acid.

5. The process of claim 4 wherein the solvent is selected from the group consisting of water, dimethylsulfoxide, N-methyl-2-pyrrolidinone, N,N-dimethylformamide, $C_1$ to $C_{10}$ alcohols, $C_2$ to $C_6$ ketones, and $C_2$ to $C_{10}$ esters.

6. The process of claim 5 wherein the solvent is water.

7. The process of claim 4 wherein the bicyclic ether is 7-oxa-bicyclo[2.2.1]hept-2-ene-1,4-dicarboxylic acid.

8. The process of claim 1 wherein the 2,5-furandicarboxyate is dimethyl 2,5-furandicarboxylate.

9. The process of claim 8 wherein the solvent is selected from the group consisting of aromatic hydrocarbons, dimethylsulfoxide, N-methyl-2-pyrrolidinone, N,N-dimethylformamide, $C_1$ to $C_{10}$ alcohols, $C_2$ to $C_6$ ketones, and $C_2$ to $C_{10}$ esters.

10. The process of claim 9 wherein the solvent is toluene.

11. The process of claim 8 wherein the wherein the bicyclic ether is dimethyl 7-oxa-bicyclo[2.2.1]hept-2-ene-1,4-dicarboxylate.

12. The process of claim 1 wherein the 2,5-furandicarboxyate is a mixture of 2,5-furandicarboxylic acid and dimethyl 2,5-furandicarboxylate.

13. The process of claim 12 wherein the solvent is selected from the group consisting of water, aromatic hydrocarbons, dimethylsulfoxide, N-methyl-2-pyrrolidinone, N,N-dimethylformamide, $C_1$ to $C_{10}$ alcohols, $C_2$ to $C_6$ ketones, $C_2$ to $C_{10}$ esters, and mixtures thereof.

14. The process of claim 1 wherein the bicyclic ether is dehydrated when the bicyclic ether is produced.

15. The process of claim 1 wherein the bicyclic ether is isolated before the bicyclic ether is dehydrated.

16. The process of claim 1 wherein the 2,5-furandicarboxylate is reacted with ethylene and the bicyclic ether is dehydrated at a temperature in the range of about 100° C. to about 250° C.

17. The process of claim 1 wherein the 2,5-furandicarboxylate is reacted with ethylene at a pressure in the range of about 10 psig to about 2000 psig.

18. The process of claim 1 wherein the 2,5-furandicarboxylate is reacted for about 60 minutes to about 480 minutes.

* * * * *